United States Patent
Bilon et al.

(10) Patent No.: US 11,045,444 B2
(45) Date of Patent: Jun. 29, 2021

(54) COMPOSITION AND METHOD FOR PROMOTING EYELASH AND EYEBROW GROWTH EXCLUSIVELY CONTAINING NATURALLY SOURCED INGREDIENTS

(71) Applicant: Plume Cosmetics Inc., Calgary (CA)

(72) Inventors: Lauren Jean Bilon, Calgary (CA); Brett Bilon, Calgary (CA); Irene Schnell, Calgary (CA)

(*) Notice: Subject to any disclaimer, the term of this patent is extended or adjusted under 35 U.S.C. 154(b) by 0 days.

(21) Appl. No.: 16/312,048

(22) PCT Filed: Jun. 28, 2017

(86) PCT No.: PCT/CA2017/050785
§ 371 (c)(1),
(2) Date: Dec. 20, 2018

(87) PCT Pub. No.: WO2018/000093
PCT Pub. Date: Jan. 4, 2018

(65) Prior Publication Data
US 2019/0224160 A1 Jul. 25, 2019

Related U.S. Application Data

(60) Provisional application No. 62/356,712, filed on Jun. 30, 2016.

(51) Int. Cl.
| | |
|---|---|
| A61K 36/53 | (2006.01) |
| A61K 31/352 | (2006.01) |
| A61Q 7/00 | (2006.01) |
| A61K 47/44 | (2017.01) |
| A61K 8/9789 | (2017.01) |
| A61K 8/49 | (2006.01) |
| A61K 8/92 | (2006.01) |
| A61K 36/52 | (2006.01) |
| A61P 17/14 | (2006.01) |
| A61P 17/00 | (2006.01) |
| A61K 36/31 | (2006.01) |
| A61K 9/00 | (2006.01) |
| A61K 36/74 | (2006.01) |
| A61K 36/28 | (2006.01) |
| A61K 8/06 | (2006.01) |
| A61Q 1/10 | (2006.01) |

(52) U.S. Cl.
CPC .............. *A61K 31/352* (2013.01); *A61K 8/06* (2013.01); *A61K 8/498* (2013.01); *A61K 8/922* (2013.01); *A61K 8/9789* (2017.08); *A61K 9/0014* (2013.01); *A61K 36/28* (2013.01); *A61K 36/31* (2013.01); *A61K 36/52* (2013.01); *A61K 36/53* (2013.01); *A61K 36/74* (2013.01); *A61K 47/44* (2013.01); *A61P 17/00* (2018.01); *A61P 17/14* (2018.01); *A61Q 7/00* (2013.01); *A61Q 1/10* (2013.01)

(58) Field of Classification Search
None
See application file for complete search history.

(56) References Cited

U.S. PATENT DOCUMENTS

| | | |
|---|---|---|
| 5,141,942 A | 8/1992 | Lal et al. |
| 5,510,113 A | 4/1996 | Bonte et al. |
| 6,960,300 B2 | 11/2005 | Majeed et al. |
| 7,300,682 B2 | 11/2007 | Majeed et al. |
| 8,911,801 B2 | 12/2014 | Debaun et al. |
| 2002/0160066 A1 | 10/2002 | Majeed et al. |
| 2004/0115249 A1 | 6/2004 | Raczek et al. |
| 2008/0241285 A1 | 10/2008 | Majeed |
| 2010/0291006 A1 | 11/2010 | Kannar et al. |
| 2011/0020302 A1 | 1/2011 | Banov et al. |
| 2012/0141390 A1 | 6/2012 | Kannar et al. |

FOREIGN PATENT DOCUMENTS

| | | | |
|---|---|---|---|
| CA | 2062745 | | 2/1991 |
| JP | 06211632 | | 8/1994 |
| JP | H09157138 | | 6/1997 |
| JP | H11292777 | | 10/1999 |
| JP | 2001206893 | A * | 7/2001 |
| JP | 2007195510 | A * | 8/2007 |
| KR | 20070080707 | | 8/2007 |
| WO | WO97/02041 | | 1/1997 |

OTHER PUBLICATIONS

Danilenko et al. (1995) American J. Pathology, vol. 147, No. 1, pp. 145-154. (Year: 1995).*
Gao et al. (2008) Food Chemistry 106: 1195-1201. (Year: 2008).*
Mandal et al. (2015) World Journal of Pharma. Res. vol. 5, Issue 1: 968-978. (Year: 2015).*
Zafar et al. (2017) Pharmcology Online, vol. 1: 11-18. (Year: 2017).*
Kavitha et al. (2010) J. Med. Plants Res. vol. 4(4): pp. 278-285. (Year: 2010).*
Park et al. (2008) J. Agric. Food Chem. 56: 10493-10497. (Year: 2008).*
International Search Report for PCT/CA2017/050785 dated Oct. 12, 2017, 4 Pages, ISA/CA, Gatineau, Quebec, Canada.
Dweck, Anthony C., Natural Preservatives, Aug. 2003, 8 Pages, Salisbury, Wiltshire, UK.
Alasbahi, Rawiya H. and Melzig, Matthias F., Plectranthus barbatus; A Review of Phytochemistry, Ethnobotanical Uses and Pharmacology—Part 2, Planta Med 2010, pp. 753-765, vol. 76.

* cited by examiner

*Primary Examiner* — Russell G Fiebig
(74) *Attorney, Agent, or Firm* — Antony C. Edwards

(57) ABSTRACT

A composition for facilitating eyelash and/or eyebrow growth which includes at least forskolin derived exclusively from *Coleus forskohlii* and at least one keratmocyte growth stimulator. In some embodiments, the keratinocyte growth stimulator may be at least one plant extract, wherein the at least one plant extract is selected from a group comprising: *Tussilago farfara* flower extract, *Achillea millefolium* extract, *Cinchona succirubra* bark extract, *Nasturtium officinale, Tropaeolum majus*. The composition may also comprise a lipid phase, comprising castor oil.

16 Claims, No Drawings

COMPOSITION AND METHOD FOR PROMOTING EYELASH AND EYEBROW GROWTH EXCLUSIVELY CONTAINING NATURALLY SOURCED INGREDIENTS

FIELD

The present disclosure relates to cosmetic compositions containing ingredients exclusively derived from natural sources, and methods for using same. More particularly, the present disclosure relates to such cosmetic compositions utilized for promoting eyelash and/or eyebrow growth.

BACKGROUND

Alopecia is a medical condition whereby hair loss occurs. Alopecia of the eyelashes or eyebrows, particularly in women, is a concern because such alopecia may have a great impact on a person's overall appearance. In many cultures, a woman's eyelashes and/or eyebrows are considered a prominent feature on a woman's face, with long and thick eyelashes being particularly prized and sought after by women. Women will go to great lengths to obtain the look and appearance of longer, fuller eyelashes, for example by applying mascara to the eyelashes, or even eyelash extensions, in a never-ending pursuit to enhance the look of one's eyelashes.

Women with missing eyelashes or short, inconsistently grown eyelashes may experience difficulty in achieving bold-looking eyelashes by mascara alone, and may choose to use extensions. However, eyelash extensions, which often involve the use of harsh adhesives to bind the extensions to the eyelid near the eyelash line, will often cause damage to the woman's natural eyelashes and thus further exacerbate the problem of short or inconsistently grown eyelashes.

Similarly, in respect to eyebrows, many women or men will seek to shape their eyebrows by various methods, such as by plucking or waxing individual eyebrow hairs so as to achieve symmetry in the appearance of the eyebrows, and/or to achieve a particular shape of each eyebrow. Some people experience alopecia of eyebrow hair, which may cause the eyebrows to look uneven or which may cause difficulty in achieving a particular shape and appearance of the eyebrows. Thus, there is a need for an effective cosmetic composition that is capable of effectively and safely promoting the growth of eyebrows and/or eyelashes.

For those who wish to grow their eyelashes and/or eyebrow hairs, there are some products available in the market incorporating prostaglandins as the active ingredient for promoting hair growth; for example, the prostaglandin bimataprost (PGF2α), otherwise referred to by its IUPAC name, 7-[3,5-dihydroxy-2-(3-hydroxy-5-phenyl-pent-1-enyl)-cyclopentyl]-N-ethyl-hept-5-enamide Examples of products available to consumers containing this ingredient, or similar prostaglandin ingredients, include Latisse® (which requires a prescription from a medical doctor), GrandeLash MD™, and Revitalash™. However, formulations for growing eyelashes containing prostaglandins have been observed to produce eyelashes which grow in odd directions and which otherwise do not look the same as eyelash hairs grown in the absence of prostaglandins. Furthermore, prostaglandins are known to cause certain side effects, such as blurred vision, eyelid redness, eye discomfort, temporary darkening of the eyelids or of the area beneath the eye and temporary burning sensation during use. Additionally, these products may cause permanent darkening of the iris.

Other pharmaceutical compositions have been devised for treating alopecia of the scalp. For example, in U.S. Pat. No. 5,141,942 issued to Lal et al, there are described pharmaceutical compositions comprising labdane diterpenoid derivatives and pyrimido(6,1-a)-isoquinolin-4-one derivatives which, when applied to mammalian skin, increased the rate of terminal hair growth on the skin. In Lal et al, it is described that labdane diterpenoid derivatives, including forskolin, are isolated from the plant *Coleus forskolii*, and teaches that pharmaceutical preparations including both the labdane diterpenoid derivatives and pyrimido(6,1-a)-isoquinolin-4-one derivatives are used for the treatment of several kinds of alopecia on the skin. However, Lal et al does not teach or suggest the application of such preparations to human eyelashes; rather, the patent merely discloses testing on the skin of baby rabbits, which testing environment radically departs from the human eye, which as noted below is particularly sensitive and requires that products applied in close proximity to the eye possess a neutral pH balance, amongst other things. In addition, Lal et al teaches that labdane diterpenoids are combined with synthetic pyrimido (6,1-a)-isoquinolin-4-one derivatives (also referred to in Lal et al as "Group B compounds") so as to produce an effective formulation for hair growth; the synthesis of such Group B compounds are described in various patent applications cited in Lal et al.

In U.S. Pat. No. 6,960,300, issued to Majeed et al, it is described that some diterpinoids, such as forskolin, are soluble in water only to concentrations of approximately 0.001%. The Majeed patent teaches that modified cyclodextrins have a much higher solubility in water than their natural counterparts, and teaches various ways of modifying cyclodextrins so as to make them more soluble. The cyclodextrins are then used for the solubilization of forskolin to obtain clear aqueous solution concentrations of 1% or greater. Although achieving increased solubility of the forskolin in aqueous solution, the Majeed patent only achieves this by adding a synthetic compound, namely modified cyclodextrins, to attain that increased solubility.

In U.S. Pat. No. 5,510,113 issued to Bonte et al, it is taught that compositions based on hydrated lipidic lamellar phases (notably liposomes), containing at least in part a derivative of labdane, including forskolin extracted from *Coleus forskolii*, may be used in cosmetic preparations for inducing hair growth on skin and increasing pigmentation of the hair. The hydrated lipidic lamellar phases, notably liposomes, are taught in Bonte to preferably include at least one amphiphilic lipid and at least one hydrophobic lipid. However, Bonte et al does not teach or suggest applying such a composition to the human eyelash line for promoting eyelash growth.

Increasingly, there is a growing concern about the use of synthetic chemicals or synthetic drugs in cosmetic preparations applied to the human body. Many are concerned about the environmental impacts caused by the production of such chemicals utilized in cosmetic products, as well as the incidental introduction of such synthetic chemicals to the environment that is caused, for example, by washing cosmetic products off the body after use or by disposing unused amounts of such products in landfills. In addition, there is concern about the side effects of introducing synthetic chemicals to the human body, as such chemicals may potentially be toxic, or some individuals may have sensitivity to a wide range of synthetic chemicals.

Many components are required for a cosmetic preparation to be sold to consumers which are designed for application to the human body. In particular, the safety of the product must be demonstrated before it may be sold in most jurisdictions. For example, cosmetic preparations must pass stringent preservative challenge testing, which establishes that the product does not allow certain types of bacteria to grow after introducing the bacteria to the product and exposing the product to conditions favourable for bacteria growth over a period of weeks. Such preservative challenge tests are necessary because cosmetic compositions will often come into contact with the human body multiple times over the lifetime of the product, and each contact with the human body may result in transfer of bacteria from the human body to the cosmetic composition, and are often stored in a bathroom environment where temperature and humidity levels are typically higher than other environments where consumer packaged goods are stored. Stringent regulations for such challenge tests exist in North America, Europe, and many other jurisdictions around the world. For example, in the United States and Europe, the standard EP or USP 51 protocol PET (Preservative Effectiveness Test) involves five different microorganisms (*Pseudomonas aeruginosa, Staph. aureus, E. coli, Candida albicans, Aspergilus brasiliensis*) introduced to the product being tested, with the test protocol requiring a reduction in the population of these organisms by a specified amount over a period of time.

Developing cosmetic preparations for application areas surrounding, and in close proximity to, the human eye, such as for example preparations designed for promoting the growth of eyelashes or eyebrow hairs, presents particular challenges because the human eyeballs and surrounding membranes are particularly sensitive as compared to the human skin on other areas of the body. In particular, formulations for application to the skin made typically have an acidic pH of 5.5 or lower, without causing irritation to the skin. In contrast, for preparations to be applied in or around the eye, such preparations have a substantially neutral pH of approximately 7, so as to avoid irritation of the eyeball and eye membranes. Respecting cosmetic preparations applied to, for example, the human eyelashes, although such cosmetics are not intended to be applied directly to the eyeball or eye membranes, a user may accidentally drip some of the cosmetic preparation into the eyeball during application. In other instances, after the preparation has been applied to the eyelash or eyebrow, a user's perspiration may cause the preparation to mix with the perspiration and thereby be transported into the eyeball or eye membrane. Thus, typical preservative ingredients for cosmetic preparations used in or near the eye include ingredients such as potassium sorbate (an irritant to skin, eyes, mucous membranes, and a respiratory irritant) or parabens (which are known carcinogens). While such ingredients are effective preservatives across a wide range of pH levels, they are synthetic chemicals and have other potential side effects as noted above.

Furthetmore, most of the natural preservative ingredients commonly known to a person skilled in the art work best in acidic environments but have little effect in neutral environments, thus requiring exponentially larger amounts of these natural preservative ingredients in order to effectively preserve the cosmetic preparation sufficient to pass the preservative challenge tests required by regulatory authorities. For example, phenyl ethyl alcohol, while a generally effective naturally-sourced preservative agent that may be extracted from certain types of flowers including rose, carnation, hyacinth, Aleppo pine, orange blossom, ylang-ylang, geranium, neroli, and champaca, due to the relatively high cost of extraction it is almost exclusively produced as a synthetic ingredient. Furthermore, phenyl ethyl alcohol is sensitizing and an eye irritant, which makes it generally unsuitable for use in cosmetics intended to be applied near the eye, due to the relatively high concentrations of phenyl ethyl alcohol required to effectively preserve a cosmetic folinulation. Phenyl ethyl alcohol also has a very intense aroma, which makes it undesirable for applications to, for example, the human eyelashes and eyebrows. Another preservative ingredient, phenoxyethanol, is a known neurotoxin and is expensive to source as a natural ingredient; as such, it is often produced synthetically as a "nature identical" ingredient. Thus, there is need for an effective, naturally-sourced preservative agent for preserving an eyelash and/or eyebrow growth serum, without the undesirable properties of other common, naturally-sourced preservative ingredients used in cosmetic formulations.

SUMMARY

In accordance with an embodiment of the present disclosure, a composition for facilitating eyelash growth comprising at least forskolin derived exclusively from *coleus forskohlii* and a keratinocyte growth stimulator is provided. In other embodiments, the keratinocyte growth stimulator comprises at least one plant extract, and the at least one plant extract may be selected from a group comprising: *Tussilago farfara* flower extract, *Achillea millefolium* extract, *Cinchona succirubra* bark extract, *Nasturtium officinale, Tropaeolum majus*. In still other embodiments, the forskolin is at a concentration of substantially 0.15% w/w.

In other embodiments, the composition may further comprise at least one preservative agent, wherein the preservative agent is a plant extract which is a non-irritant when in proximity to the human eye. In some embodiments, the preservative agent may comprise *Carya ovata*.

In other embodiments, the composition is an emulsion adapted to be further applied to a human eyelash line and/or to a human eyebrow, so as to transport the at least forskolin and the keratinocyte growth stimulator to one or more eyelash roots and/or eyebrow hair roots of the eyelash line and/or eyebrow. In still other embodiments, the emulsion comprises an aqueous phase comprising the keratinocyte growth stimulators and a lipid phase comprising the forskolin. In some embodiments, the lipid phase comprises castor oil. In some embodiments, the composition is adapted to transition from a visible appearance to an invisible appearance when applied to the eyelash line and/or eyebrow as the composition dries.

In some embodiments of the present disclosure, a method of using the composition comprises applying the composition to a human eyelash line and/or to a human eyebrow. In other embodiments, the method of using the composition further comprises applying the composition to the human eyelash line and/or the human eyebrow at least one per day.

In some embodiments of the present disclosure, a composition is provided for facilitating eyelash growth comprising forskolin derived exclusively from *Coleus forskohlii* and a lipid phase so as to transport the forskolin to one or more eyelash hair roots, the lipid phase comprising castor oil. In other embodiments, the composition further comprises an aqueous phase, the aqueous phase comprising a keratinocyte growth stimulator. In yet other embodiments of the present disclosure, the composition described in this paragraph is an emulsion.

DETAILED DESCRIPTION

In this disclosure, there are taught various cosmetic preparations which exclusively contain naturally derived ingredients and which are effective for treating alopecia of the eyelashes and eyebrows, and for improving the quality and length of eyelash and eyebrow hairs.

In some embodiments of the present disclosure, the compositions include forskolin exclusively derived from the plant *Coleus forskolii*, which effectively promotes the growth of eyelash and eyebrow hairs. Without intending to be limiting, it is believed by the applicant that the forskolin ingredient acts as an adenylate cyclase activator. In some embodiments, the composition may contain concentrations of forskolin at substantially 0.15% w/w, although persons skilled in the art will understand that other concentrations of forskolin may also be effective at promoting eyelash and/or eyebrow growth and are within the scope of this present disclosure. Advantageously, in some embodiments the composition includes a lipid phase which acts as a vehicle for transporting the forskolin to the roots of the eyelash hair or eyebrow hair for which the user of the composition desires to stimulate hair growth.

As noted above, forskolin is known to be substantially insoluble in water, which makes it difficult to deliver forskolin to hair roots in an aqueous phase, generally requiring a synthetic additive, such as modified cyclodextrins, to increase the solubilizaton of the forskolin ingredient for delivery in an aqueous medium. In some embodiments of this disclosure the composition comprises an emulsion including a lipid phase and an aqueous phase; in other embodiments of the present disclosure, the lipid phase advantageously comprises castor oil, which is previously known to promote and stimulate hair growth due to the composition of castor oil containing approximately 90% ricinoleic acid, which substance is known to stimulate production of prostaglandins by the human body when applied to the scalp.

It is postulated by the Applicant, without committing to any particular theory of the synergistic mechanism, that utilizing castor oil as the lipid phase for transporting forskolin in a cosmetic formulation, in addition to providing a suitable vehicle for transporting the forskolin ingredient to the targeted hair roots, additionally boosts the hair growth stimulation effect of the forskolin ingredient by stimulating the body's natural production of prostaglandins, by hydrating the hair shaft due to the alpha end of the ricinoleic acid molecule being an omega 9 fatty acid, and furthermore, the polar nature of the castor oil may act as a bridge between the *Coleus forskolii* oil extract and the roots of the eyelashes or eyebrows. Notably, the Applicant's composition disclosed herein avoids the need for synthetic additives so as to solubilize the forskolin, instead providing a lipid phase suitable for delivering the forskolin to the targeted hair roots of the eyelashes or eyebrows, advantageously providing a composition that is comprised entirely of naturally-derived ingredients.

In other embodiments of the present disclosure, the compositions also include various other plant extracts that enhance the composition's hair growth properties by stimulating the growth of keratinocytes and associated keratins for the formation of eyelash and/or eyebrow hairs (herein, these types of ingredients are individually and collectively referred to as "keratinocyte growth stimulators"). For example, not intended to be limiting, some embodiments may include one or more of the following compounds or extracts naturally derived from plant sources: *Tussilago farfara* flower extract, *Achillea millefolium* extract, *Cinchona succirubra* bark extract, *Nasturtium officinale* and/or *Tropaeolum majus*, at a total combined concentration of the keratinocyte growth stimulators in the range of substantially 12.5%. For example, not intended in any way to be limiting, an eyelash and eyebrow growth serum may be formulated with forskolin extract at 0.15% w/w, Cressatine® at 2.5% w/w, which is a cosmetic ingredient distributed by Solabia™ containing *Nasturtium officinale* and *Tropaeolum majus* extracts in aqueous solution, and Tricorexina® at 10% w/w, which is another cosmetic ingredient distributed by Res Pharma™ containing *Tussilago Farfara* flower, *Achillea Millefolium* and *Succirubra* Bark extracts in aqueous solution. A person skilled in the art would appreciate that other concentration ranges of the keratinocyte growth stimulator ingredients listed above would also be effective at promoting the growth of eyelashes and/or eyebrow hairs and would fall within the scope of the present disclosure.

The above example of an eyelash and eyebrow serum formulation is not intended to be limiting, and a person skilled in the art will appreciate that other keratinocyte growth stimulators which are naturally derived and which stimulate the growth of keratinocytes and associated keratins for the formation of eyelash and/or eyebrow hair may be effective and that such other keratinocyte growth stimulators, used in combination with forskolin, are also within the scope of the present disclosure.

Although the keratinocyte growth stimulators are generally known to a person skilled in the art for promoting hair growth, surprisingly, the Applicant found that such active ingredients, when used alone in combination with various excipients, were not very effective in promoting eyelash growth. However, surprisingly, the combination of forskolin with keratinocyte growth stimulators in cosmetic preparations were found, during testing, to be highly effective in growing longer, healthier, fuller-looking eyelashes than any other cosmetic preparation that did not include forskolin. For example, the Applicant tested a formulation including forskolin in combination with *Tussilago forfora* flower extract, *Achillea millefolium* extract, *Cinchona succirulora* bark extract, *Nasturtium officinale* and *Tropaeolum majus*.

In one test, approximately 60 women were provided with the aforementioned formulation and asked to apply the formulation to their eyelash lines at least once per day for a period of approximately 6 to 8 weeks. These women were also asked to take photographs before the first date of application and on the last date of application, so as to provide a visual measurement of the eyelash growth during the test period. Surprisingly, it was found that about 58 of the 60 test group participants experienced eyelash growth, of between approximately 20% to 50%, after applying the eyelash serum to each eye at least once per day for a period of approximately 6 to 8 weeks, based on a visual comparison of "before and after" photographs taken by the test group participants prior to the testing period and at the end of the testing period. In addition, the test group participants found that the thickness and density of the eyelash hairs appeared to increase as a result of using the formulation over the period of 6 to 8 weeks, again based on a visual comparison of the before and after photographs taken by the test participants of their eyelashes. In a similar test, a test group of approximately 10 women applied a different composition including all of the active ingredients listed above except for forskolin, and it was found that any change in the length of the eyelash hairs was negligible, after daily application of this formulation by the 10 women for a period of approximately 6 to 8 weeks (again, based on a visual comparison of "before and after" photographs taken by the test group participants prior to the testing period and at the end of the testing period).

Throughout this specification, in which the Applicant refers to applying the cosmetic composition of the various embodiments of this disclosure to the "eyelash line," this phrase is intended to refer to the edge of eyelid from which eyelash hairs protrude. Advantageously, in some embodiments of the present invention the composition, when initially applied to the eyelash line or eyebrow, is milky-white in appearance until it dries, at which point the composition becomes invisible to the human eye. This feature of the composition enables the user to visually determine whether the composition has been adequately applied to all portions of the eyelash line or eyebrow, so as to effectively deliver the active ingredients to the eyelash or eyebrow roots and thereby increase the overall effectiveness of the composition in promoting eyelash or eyebrow growth across the entire eyelash line or eyebrow. Furthermore, the composition advantageously becomes invisible within substantially one or more minutes of applying the composition to the eyelash line, as the initial milky-white appearance of the composition may otherwise be considered aesthetically displeasing.

In some embodiments of the present disclosure, *Carya ovata*, otherwise known as hickory bark extract, is a naturally-sourced ingredient that acts as an effective preservative for a cosmetic composition exclusively comprised of all naturally-sourced ingredients. Persons ordinarily skilled in the art are primarily familiar with hickory bark extract as a perfuming agent. However, the Applicant found that, surprisingly, *Carya ovata* in combination with forskolin, which is also an antimicrobial agent, are sufficient to pass the strict bacterial loading preservative challenge tests required by regulatory agencies. A concentration range substantially in the range of 10% w/w was found by the Applicant to be effective as a preservative in a cosmetic formulation prepared in accordance with this present disclosure, sufficient to pass the preservative challenge tests mandated in Europe, Canada and the United States for that product. However, it is understood by persons skilled in the art that other concentrations of the *Carya ovata* ingredient may also be effective and fall within this present disclosure.

A person skilled in the art will appreciate that other compositions containing at least forskilin exclusively derived from the *Coleus forskolii* plant for promoting the growth of human eyelashes are within the scope of the present disclosure, and that this disclosure is not limited to the examples of compositions described above.

What is claimed is:

1. A topical cosmetic composition for promoting eyelash growth comprising effective amounts of: (a) forskolin extracted from *Coleus forskohlii*; and (b) a keratinocyte growth stimulator, wherein the composition is an emulsion having an aqueous phase containing the said keratinocyte growth stimulator and a lipid phase containing said forskolin and wherein the emulsion transports the forskolin and the keratinocyte growth stimulator to one or more eyelash roots of a human eyelash line when the emulsion is applied to the human eyelash line so as to facilitate eyelash growth.

2. The composition of claim 1, wherein the keratinocyte growth stimulator comprises at least one plant extract.

3. The composition of claim 2, wherein the at least one plant extract is selected from a group comprising: *Tussilago farfara* flower extract, *Achillea millefolium* extract, *Cinchona succirubra* bark extract, *Nasturtium officinale*, *Tropaeolum majus*.

4. The composition of claim 1, further comprising at least one preservative agent wherein the at least one preservative agent is a second plant extract.

5. The composition of claim 4, wherein the second plant extract is a non-irritant when in proximity to the human eye.

6. The composition of claim 4, wherein the second plant extract comprises *Carya ovata*.

7. The composition of claim 1, wherein the forskolin is at a concentration of 0.15% w/w.

8. The composition of claim 1, wherein the lipid phase comprises castor oil.

9. The composition of claim 1, wherein the composition transitions from a visible appearance to an invisible appearance when applied to said eyelash line as the composition dries.

10. The composition of claim 1, wherein the keratinocyte growth stimulator is at a concentration of 12.5% w/w.

11. The composition of claim 6, wherein the *Carya ovata* is at a concentration of 10% w/w.

12. A method of using the composition of claim 1, comprising applying the composition to a human eyelash line.

13. The method of claim 12, further comprising applying the composition to the human eyelash line at least once per day.

14. A topical cosmetic composition for promoting eyebrow growth comprising effective amounts of: (a) forskolin extracted from *Coleus forskohlii*; and (b) a keratinocyte growth stimulator, wherein the composition is an emulsion having an aqueous phase containing the said keratinocyte growth stimulator and a lipid phase containing said forskolin and wherein the emulsion transports the forskolin and the keratinocyte growth stimulator to one or more eyebrow hair roots of a human eyebrow when the emulsion is applied to the human eyebrow so as to facilitate eyebrow growth.

15. A method of using the composition of claim 14, comprising applying the composition to a human eyebrow.

16. The method of claim 15, further comprising applying the composition to the human eyebrow at least once per day.

* * * * *